United States Patent
Lin et al.

(10) Patent No.: US 10,009,848 B2
(45) Date of Patent: Jun. 26, 2018

(54) POWER ADJUSTING MODULE AND WEARABLE DEVICE EMPLOYING SAME

(71) Applicant: Chiun Mai Communication Systems, Inc., New Taipei (TW)

(72) Inventors: Yen-Hui Lin, New Taipei (TW); Chien-Chang Liu, New Taipei (TW)

(73) Assignee: Chiun Mai Communication Systems, Inc., New Taipei (TW)

( * ) Notice: Subject to any disclaimer, the term of this patent is extended or adjusted under 35 U.S.C. 154(b) by 63 days.

(21) Appl. No.: 15/199,992

(22) Filed: Jul. 1, 2016

(65) Prior Publication Data

US 2017/0181093 A1    Jun. 22, 2017

(30) Foreign Application Priority Data

Dec. 21, 2015 (CN) .......................... 2015 1 0962766

(51) Int. Cl.
| | | |
|---|---|---|
| *H04L 12/26* | (2006.01) | |
| *H04W 52/02* | (2009.01) | |
| *A61B 5/024* | (2006.01) | |
| *A61B 5/0402* | (2006.01) | |
| *A61B 5/00* | (2006.01) | |

(Continued)

(52) U.S. Cl.
CPC ..... *H04W 52/0254* (2013.01); *A61B 5/02433* (2013.01); *A61B 5/0402* (2013.01); *A61B 5/681* (2013.01); *G06F 1/163* (2013.01); *G06F 1/1694* (2013.01); *H04M 1/026* (2013.01); *A61B 2562/0219* (2013.01); *Y02D 70/00* (2018.01); *Y02D 70/26* (2018.01)

(58) Field of Classification Search
CPC .......... H04L 2012/5608; H04W 84/12; H04W 88/08; H04W 80/04; H04W 88/06; H04W 84/18; H04W 74/08; H04W 52/0254; A61B 5/02433; A61B 5/0402; A61B 5/681; A61B 2562/0219; G06F 1/163; G06F 1/1694; H04M 1/026; Y02D 70/26; Y02D 70/00
USPC .............. 370/310.2, 328, 338, 311, 252, 339
See application file for complete search history.

(56) References Cited

U.S. PATENT DOCUMENTS

| | | | | |
|---|---|---|---|---|
| 8,852,097 | B2 * | 10/2014 | Shimada ............. | G06F 19/3406 600/300 |
| 9,411,456 | B2 * | 8/2016 | Meer ........................ | G09G 3/20 |

(Continued)

FOREIGN PATENT DOCUMENTS

| | | |
|---|---|---|
| TW | 201203695 A | 1/2012 |
| TW | I443548 | 7/2014 |

OTHER PUBLICATIONS

US 9,798,374, 10/2017, Tu (withdrawn)*

*Primary Examiner* — Brenda H Pham
(74) *Attorney, Agent, or Firm* — ScienBiziP, P.C.

(57) ABSTRACT

A power adjusting module applied in a wearable device and includes a sensor, a central processing unit (CPU). The sensor triggers a detect signal. The CPU determines if the wearable device is in a wearing mode or a free mode according to the detect signal. If the wearable device is determined in a wearing mode, the CPU generates an instruction for increasing a transmission power of an antenna of the wearable device; if the wearable device is determined in a free mode, the CPU generates an instruction for decreasing the transmission power of the antenna. A wearable device employing the power adjusting module is also provided.

17 Claims, 2 Drawing Sheets

(51) Int. Cl.
*G06F 1/16* (2006.01)
*H04M 1/02* (2006.01)

(56) References Cited

U.S. PATENT DOCUMENTS

| | | | | |
|---|---|---|---|---|
| 2010/0271187 A1* | 10/2010 | Uysal | ................... | G06K 7/0008 340/10.4 |
| 2013/0324072 A1* | 12/2013 | Hsu | ........................ | H04W 4/22 455/404.2 |
| 2015/0135310 A1* | 5/2015 | Lee | ........................ | A61B 5/681 726/20 |
| 2015/0187206 A1* | 7/2015 | Saurin | .................... | G08C 17/02 340/5.61 |

* cited by examiner

POWER ADJUSTING MODULE AND WEARABLE DEVICE EMPLOYING SAME

FIELD

The subject matter herein generally relates to a power adjusting module and a wearable device employing the power adjusting module.

BACKGROUND

Wearable devices need to be processed a specific absorption rate (SAR) test when manufactured. Decreasing a radiating power of an antenna of the wearable device, maintaining a radiating efficiency, and meeting a SAR test standard are still problems to be solved in the art.

BRIEF DESCRIPTION OF THE DRAWINGS

Many aspects of the disclosure can be better understood with reference to the following figures. The components in the figures are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
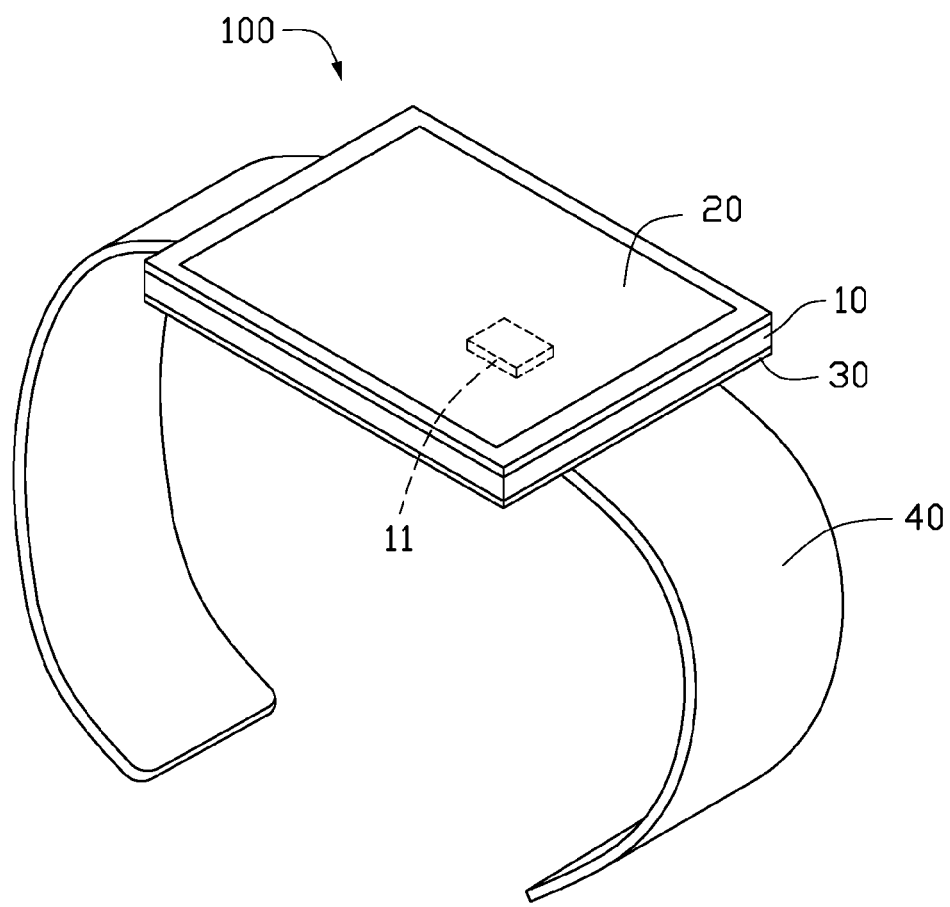
FIG. 1 is an isometric view of one embodiment of a wearable device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series and the like.

FIG. 1 illustrates one embodiment of a wearable device 100 can be coupled to a wrist of a user. The wearable device 100 can be a watch and a bracelet. The wearable device 100 includes a body 10, a screen 20, a cover 30 and a wearable portion 40.

The screen 20 and the cover 30 are arranged on opposite sides of the body 10. The wearable portion 40 may be coupled to the cover 30 and extended from opposite ends of the cover 30. The wearable portion 40 is detachably worn to the wrist of the user, while the screen 20 faces to the user for providing information.

Figure 2:
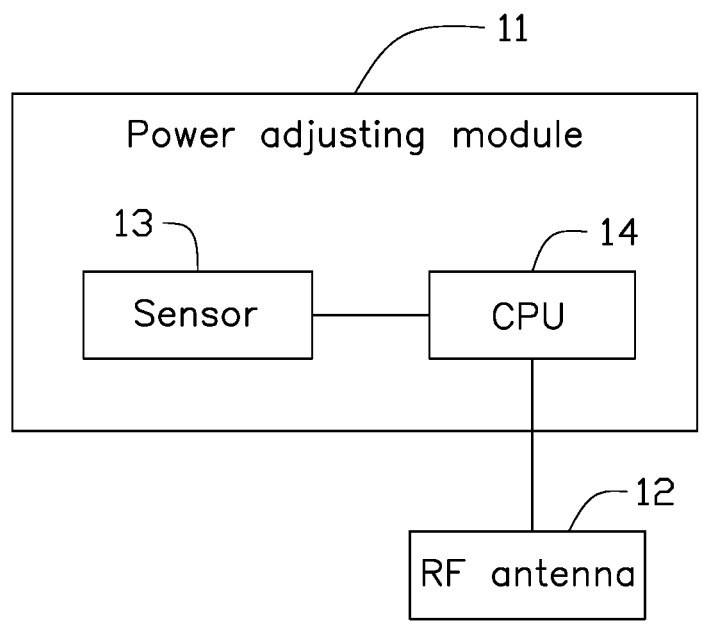
FIG. 2 is a block diagram of one embodiment of a power adjusting module.

FIG. 2 illustrates that the wearable device 100 further includes a power adjusting module 11 and a radio frequency (RF) antenna 12. The power adjusting module 11 includes a sensor 13 and a central processing unit (CPU) 14. The RF antenna 12 is configured for transmitting and receiving RF signals. The sensor 13 is configured for triggering a detect signal and transmitting to the CPU 14. The CPU 14 is configured for determining if the wearable device 100 is in a wearing mode or a free mode according to the detect signal. If the wearable device 100 is in the wearing mode, the CPU 14 controls the RF antenna 12 to increase a transmission power. If the wearable device 100 is in the free mode, the CPU 14 controls the RF antenna 12 to decrease a transmission power. In at least one embodiment, the RF antenna 12, the sensor 13 and the CPU 14 can be received in the body 10. In other embodiments, the RF antenna 12 can be integrated with the cover 30 which is made of metal material; the sensor 13 can be coupled to the cover 30.

In a first embodiment, the sensor 13 is a gravity sensor configured for detecting acceleration of the wearable device and the detect signal is an acceleration signal. When the wearable device 100 is worn by the user, the sensor 13 may generate different acceleration signals according to movements of the user and further transmits the acceleration signals to the CPU 14. The CPU 14 determines the wearable device 100 is in the wearing mode according to the acceleration signals. When the wearable device 100 is not worn by the user, the sensor 13 may not trigger acceleration signals since the wearable device 100 is not moved with the user. The CPU 14 may not receive any acceleration signal and determines the wearable device 100 is in the free mode.

In a second embodiment, the sensor 13 is a light sensor, which includes a light emitting diode (LED) and a light receiver. The LED is configured for transmitting light toward the wrist wearing the wearable device 100 and the light receiver is configured for receiving light reflected from the wrist. When the user is wearing the wearable device 100, the wrist may block the light path transmitted by the LED, the light receiver receives the reflected lights reflected by the wrist and transmits an electronic signal to the CPU 14. The CPU 14 determines the wearable device 100 is in the wearing mode according to the electronic signal. When the user is not wearing the wearable device 100, the light receiver may not receive reflected lights, then the CPU 14 may not receive any signals from the sensor 13 and determines the wearable device 100 is in the free mode.

In a third embodiment, the sensor 13 is a pulse wave sensor, such as an infrared pulse wave sensor and a photoelectric pulse wave sensor. The pulse wave sensor includes an infrared LED and an infrared photo transistor. The infrared LED is configured for transmitting infrared ray toward the wrist wearing the wearable device 100. When the user is wearing the wearable device 100, the wrist may block the infrared ray transmitted by the infrared LED, when the infrared ray reach blood vessels of the wrist and part of the infrared ray may be reflected by the blood vessels, the infrared photo transistor receives the reflected infrared ray reflected by the blood vessels and transmits an electronic signal to the CPU 14. The CPU 14 determines the wearable device 100 is in the wearing mode according to the electronic signal. When the user is not wearing the wearable device 100, the infrared photo transistor may not receive reflected infrared ray, then the CPU 14 may not receive any signals from the sensor 13 and determines the wearable device 100 is in the free mode.

In a fourth embodiment, the sensor 13 is a cardiogram sensor, which includes an electrode tab arranged on the cover 30. When the user is wearing the wearable device 100, the wrist contacts the electrode tab on the cover 30, the electrode tab detects movement electric potential of the heart of the user and the sensor 13 transmits an electronic signal to the CPU 14 according to the detected movement electric potential signal. The CPU 14 determines the wearable device 100 is in the wearing mode according to the electronic signal. When the user is not wearing the wearable device 100, the sensor 13 may not detect any movement electric potential signal, then the CPU 14 may not receive any signals from the sensor 13 and determines the wearable device 100 is in the free mode.

The wearable device 100 may use only one of the aforesaid sensors 13 or a combination of the sensor 13 to trigger the detect signals. If wearable device 100 uses multiple sensors 13, when all the sensors 13 and the CPU 14 determine a same result for the wearing mode or the free mode, the determination is valid. When the sensors 13 and the CPU 14 determine different result for the wearing mode or the free mode, the determination is invalid, the sensors 13 and the CPU 14 may restart determining again.

The wearable device 100 includes the sensor 13 and the CPU 14 for determining if the wearable device 100 is in the wearing mode or in the free mode, thus to adjust the transmission power of the RF antenna 12 according to the status of the wearable device 100, thereby maintaining a radiating efficiency and meeting a specific absorption rate (SAR) test standard.

It is believed that the embodiments and their advantages will be understood from the foregoing description, and it will be apparent that various changes may be made thereto without departing from the scope of the disclosure or sacrificing all of its advantages, the examples hereinbefore described merely being illustrative embodiments of the disclosure.

What is claimed is:

1. A power adjusting module applied in a wearable device, the power adjusting module comprising:
    a sensor configured for triggering a detect signal; and
        a central processing unit (CPU) configured for determining if the wearable device is in a wearing mode or a free mode according to the detect signal;
        wherein if the wearable device is determined in a wearing mode, the CPU generates an instruction for increasing a transmission power of an antenna of the wearable device; and
        wherein if the wearable device is determined in a free mode, the CPU generates an instruction for decreasing the transmission power of the antenna;
        wherein the sensor comprises a pulse wave sensor configured for transmitting infrared ray and detecting whether the infrared ray is blocked; and
        wherein the pulse wave sensor includes an infrared LED and an infrared photo transistor, when the user is wearing the wearable device, the infrared LED transmits infrared ray toward a wrist of a user and is reflected by blood vessels of the wrist, the infrared photo transistor receives the reflected infrared ray and transmits an electronic signal to the CPU, the CPU determines the wearable device is in the wearing mode according to the electronic signal; when the wearable device is not worn by the user, the pulse wave sensor does not trigger detect signals and the CPU determines the wearable device is in the free mode.

2. The power adjusting module as claimed in claim 1, wherein the sensor comprises a gravity sensor configured for detecting acceleration of the wearable device.

3. The power adjusting module as claimed in claim 2, wherein when the wearable device is worn by a user, the gravity sensor generates different acceleration signals according to movements of the user and further transmits the acceleration signals to the CPU, the CPU determines the wearable device is in the wearing mode according to the acceleration signals; when the wearable device is not worn by the user, the gravity sensor does not trigger detect signals and the CPU determines the wearable device is in the free mode.

4. The power adjusting module as claimed in claim 1, wherein the sensor comprises a light sensor configured for transmitting light and detecting whether the light path is blocked.

5. The power adjusting module as claimed in claim 4, wherein the light sensor further comprises a light emitting diode (LED) and a light receiver, when the user is wearing the wearable device, the LED transmits light which is blocked by a wrist of a user, the light receiver receives the light reflected by the wrist and transmits an electronic signal to the CPU, the CPU determines the wearable device is in the wearing mode according to the electronic signal; when the wearable device is not worn by the user, the light sensor does not trigger detect signals and the CPU determines the wearable device is in the free mode.

6. The power adjusting module as claimed in claim 1, wherein the sensor comprises a cardiogram sensor configured for contacting a wrist of a user and detecting movement electric potential of the heart of the user.

7. The power adjusting module as claimed in claim 6, wherein when the user is wearing the wearable device, the cardiogram sensor detects movement electric potential of the heart and transmits an electronic signal to the CPU, the CPU determines the wearable device is in the wearing mode according to the electronic signal; when the wearable device is not worn by the user, the cardiogram sensor does not trigger detect signals and the CPU determines the wearable device is in the free mode.

8. A wearing device detachably coupled to a wrist of a user, the wearing device comprising:
    a radio frequency (RF) antenna configured for transmitting and receiving RF signals;
    a sensor configured for triggering a detect signal; and
    a central processing unit (CPU) configured for determining if the wearable device is in a wearing mode or a free mode according to the detect signal;
    wherein if the wearable device is determined in a wearing mode, the CPU generates an instruction for increasing a transmission power of the RF antenna; and wherein if the wearable device is determined in a free mode, the CPU generates an instruction for decreasing the transmission power of the RF antenna;
    wherein the sensor comprises a pulse wave sensor configured for transmitting infrared ray and detecting whether the infrared ray is blocked; and
    wherein the pulse wave sensor includes an infrared LED and an infrared photo transistor, when the user is wearing the wearable device, the infrared LED transmits infrared ray toward a wrist of a user and is reflected by blood vessels of the wrist, the photo transistor receives the reflected infrared ray and transmits an electronic signal to the CPU, the CPU determines the wearable device is in the wearing mode according to the electronic signal; when the wearable device is not worn by the user, the pulse wave sensor does not trigger detect signals and the CPU determines the wearable device is in the free mode.

9. The wearable device as claimed in claim 8, further comprising a body, a screen and a cover, wherein the RF antenna, the sensor and the CPU are received in the body, the screen and the cover are arranged to opposite sides of the body.

10. The wearable device as claimed in claim 9, further comprising a wearable portion, wherein the wearable portion is coupled to the cover and extended from opposite ends of the cover, the wearable portion is detachably worn to the wrist of the user, while the screen faces to the user for providing information.

11. The wearable device as claimed in claim 8, wherein the sensor comprises a gravity sensor configured for detecting acceleration of the wearable device.

12. The wearable device as claimed in claim 11, wherein when the wearable device is worn by a user, the gravity sensor generates different acceleration signals according to movements of the user and further transmits the acceleration signals to the CPU, the CPU determines the wearable device is in the wearing mode according to the acceleration signals; when the wearable device is not worn by the user, the gravity sensor does not trigger detect signals and the CPU determines the wearable device is in the free mode.

13. The wearable device as claimed in claim 8, wherein the sensor comprises a light sensor configured for transmitting light and detecting whether the light path is blocked.

14. The wearable device as claimed in claim 13, wherein the light sensor further comprises a light emitting diode (LED) and a light receiver, when the user is wearing the wearable device, the LED transmits light which is blocked by a wrist of a user, the light receiver receives the light reflected by the wrist and transmits an electronic signal to the CPU, the CPU determines the wearable device is in the wearing mode according to the electronic signal; when the wearable device is not worn by the user, the light sensor does not trigger detect signals and the CPU determines the wearable device is in the free mode.

15. The wearable device as claimed in claim 8, wherein the sensor comprises a cardiogram sensor configured for contacting a wrist of a user and detecting movement electric potential of the heart of the user.

16. The wearable device as claimed in claim 15, wherein when the user is wearing the wearable device, the cardiogram sensor detects movement electric potential of the heart and transmits an electronic signal to the CPU, the CPU determines the wearable device is in the wearing mode according to the electronic signal; when the wearable device is not worn by the user, the cardiogram sensor does not trigger detect signals and the CPU determines the wearable device is in the free mode.

17. A wearing device detachably coupled to a wrist of a user, the wearing device comprising:
    a radio frequency (RF) antenna configured for transmitting and receiving RF signals;
    a sensor configured for triggering a detect signal; and
    a central processing unit (CPU) configured for determining if the wearable device is in a wearing mode or a free mode according to the detect signal;
    wherein if the wearable device is determined in a wearing mode, the CPU generates an instruction for increasing a transmission power of the RF antenna; and wherein if the wearable device is determined in a free mode, the CPU generates an instruction for decreasing the transmission power of the RF antenna;
    wherein the sensor comprises a cardiogram sensor configured for contacting a wrist of a user and detecting movement electric potential of the heart of the user;
    wherein when the user is wearing the wearable device, the cardiogram sensor detects movement electric potential of the heart and transmits an electronic signal to the CPU, the CPU determines the wearable device is in the wearing mode according to the electronic signal; when the wearable device is not worn by the user, the cardiogram sensor does not trigger detect signals and the CPU determines the wearable device is in the free mode.

\* \* \* \* \*